US006421558B1

(12) United States Patent
Huey et al.

(10) Patent No.: US 6,421,558 B1
(45) Date of Patent: Jul. 16, 2002

(54) UTERINE ACTIVITY MONITOR AND METHOD OF THE SAME

(75) Inventors: Raymond J. Huey, Orange; William Kosturko, Milford; Charles A. Reynolds, West Haven, all of CT (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/606,707

(22) Filed: Jun. 29, 2000

(51) Int. Cl.$^7$ ................................................ A61B 5/04
(52) U.S. Cl. ........................................................ 600/546
(58) Field of Search ................................. 600/546, 588, 600/300, 587; 607/20, 28, 25, 26

(56) References Cited

U.S. PATENT DOCUMENTS

| | | | |
|---|---|---|---|
| 4,256,118 A | * | 3/1981 | Nagel .......................... 600/546 |
| 5,301,680 A | | 4/1994 | Rosenberg |
| 5,397,344 A | | 3/1995 | Garfield et al. |
| 5,450,857 A | | 9/1995 | Garfield et al. |
| 5,483,970 A | | 1/1996 | Rosenberg |
| 5,546,953 A | | 8/1996 | Garfield |
| 5,623,939 A | | 4/1997 | Garfield |
| 5,776,073 A | | 7/1998 | Garfield et al. |
| 5,785,664 A | | 7/1998 | Rosenberg |
| 5,800,470 A | * | 9/1998 | Stein et al. .................... 607/20 |

OTHER PUBLICATIONS

Chwalisz, et al., "Basic Mechanisms Controlling Term and Preterm Birth", Ernst Schering Research Foundation Workshop 7, 1994, pp. 1–28.

Garfield, et al., "Control and assessment of the uterus . . . ", Human Reproduction Update 1988, vol. 4, No. 5, pp. 673–695.

Buhimschi, et al., "Electrical Activity of the Human Uterus During Pregnancy as Recorded from the Abdominal Surface", Obstetrics and Gynecology, vol. 90, No. 1; 1997; pp. 102–111.

M. L. Rudee, "Gap Junctions: Their Presence and Necessity in Myometrium During Parturition", Science, vol. 198, 1977, pp. 958–960.

Garfield, et al., "Instrumentation for the diagnosis of term and preterm labour", Journal of Perinatal Medicine, 1998, pp. 413–436.

Garfield, et al., "Control of Uterine Contractility", CRC Press, 1994, pp. 41–79.

Brown, et al., "A Randomized Comparison of Home Uterine Activity . . . Preterm Labor", Copyright 1999 by Mosby Co., Inc., pp. 798–898.

* cited by examiner

*Primary Examiner*—Kevin Shaver
*Assistant Examiner*—Brian Szmal
(74) *Attorney, Agent, or Firm*—Michael Best & Friedrich LLP

(57) ABSTRACT

A method and apparatus for generating a signal representing uterine activity. The method including the acts of obtaining a uterine electromyography (EMG) signal, and processing the uterine EMG signal to produce a signal representative of uterine activity. The apparatus including a sensor for acquiring a uterine electromyography (EMG) signal, and a signal processor for generating a signal representative of uterine activity in response to the uterine EMG signal.

44 Claims, 3 Drawing Sheets

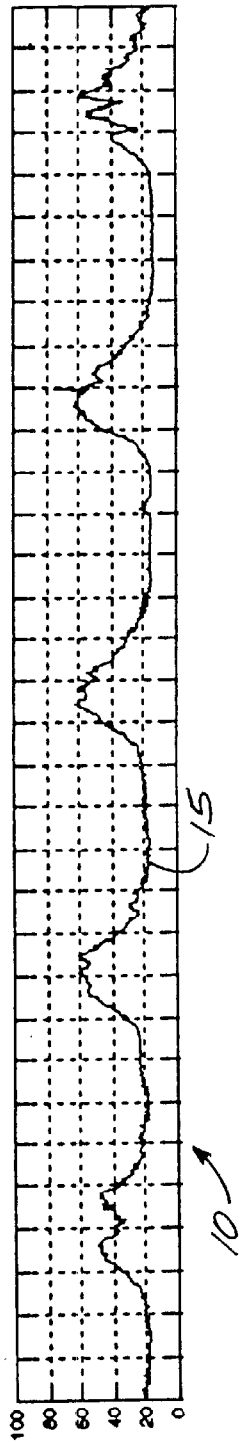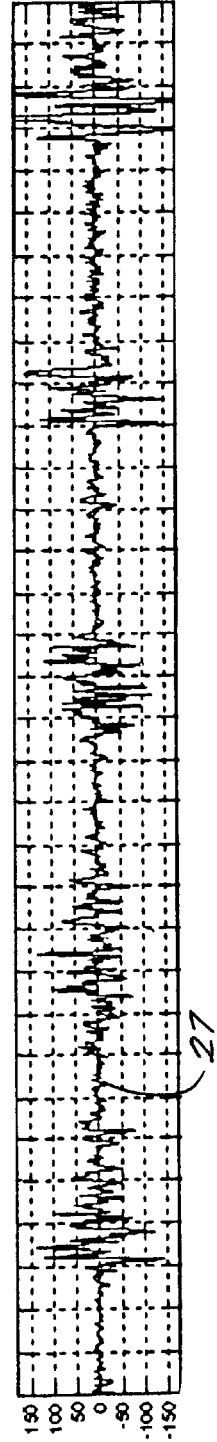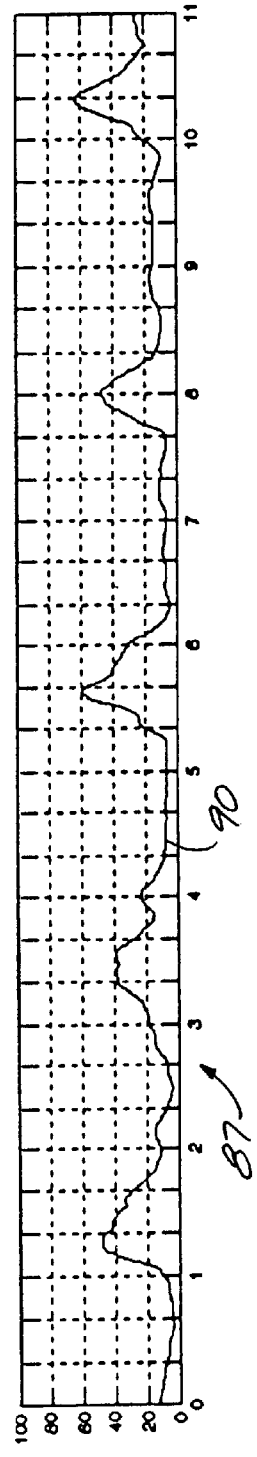

UTERINE ACTIVITY MONITOR AND METHOD OF THE SAME

BACKGROUND OF THE INVENTION

The invention relates to a method and apparatus for generating a signal representing uterine activity, and particularly to a monitor for obtaining and processing a uterine electromyography signal to produce a signal representative of uterine activity.

Uterine activity and fetal heart rate are two primary parameters measured in fetal monitoring during birth delivery. Current practice uses two methods to measure uterine activity. The first method is internal to the patient and uses an intrauterine pressure sensor (hereinafter referred to as a "IUP" sensor). The IUP sensor is an invasive device that can only be used after rupturing membranes. The IUP sensor produces an output that is a true function of uterine pressure and monitors contraction frequency and contraction duration. The second method is external to the patient and uses a tocodynamometer (hereinafter referred to as "toco"). The toco is a non-invasive device that is placed on the maternal abdomen and is secured with an elastic belt or strap. The toco does not provide any information representative of uterine pressure, and is used to monitor contraction frequency and contraction duration. The output from the IUP sensor or the toco is processed by the fetal monitor and is printed or displayed on a uterine activity chart. An example uterine activity chart is shown in FIG. 1 where the uterine activity chart 10 displays a uterine activity waveform 15 resulting from a processed toco signal.

SUMMARY OF THE INVENTION

Uterine contractions are the result of coordinated contractions by individual myometrial cells of the uterus. At the cellular level, the contractions are triggered by an action potential. The action potential is a voltage signal that can be measured as an electromyography (hereinafter referred to as "EMG") signal. During pregnancy, cellular electrical connectivity increases such that the action potential propagates to produce a coordinated contraction involving the entire uterus. The action potential during a uterine contraction can be measured with electrodes placed on the maternal abdomen resulting in a uterine EMG signal. The EMG signal is then processed to produce a signal that is functionally equivalent to a uterine activity signal created by a toco. The equivalent uterine activity signal provides contraction frequency and contraction duration information. In addition, the EMG signal approximates at least one component that would be acquired by an IUP sensor.

Accordingly, the invention provides a monitor. The monitor includes a sensor for acquiring a uterine EMG signal and a signal processor for generating a signal representative of uterine activity in response to the uterine EMG signal. The signal representative of uterine activity indicates uterine contraction frequency and contraction duration information. Additionally, the signal representative of uterine activity approximates a signal that would be acquired using either a toco or approximates at least one component of a signal that would be acquired using an IUP sensor.

In a first embodiment, the signal processor includes a receiver that receives the uterine EMG signal from the sensor and generates an analog signal representative of uterine activity. The signal processor further includes a microprocessor electrically connected to the receiver for receiving the analog signal representative of uterine activity and converting the analog signal representative of uterine activity into a digital signal representative of uterine activity. The signal processor also includes a memory unit electrically connected to the microprocessor for storing the digital signal representative of uterine activity.

In a second embodiment, the signal processor includes a microprocessor that receives the uterine EMG signal and generates a signal representative of uterine activity. The received uterine EMG signal can be a signal that is received directly from the sensor or can be a uterine EMG signal that has be processed by an amplifier and band-pass filter. The microprocessor includes software to perform digital signal processing techniques on the received uterine EMG signal.

The invention further provides a method of generating a signal representing uterine activity. The method includes the acts of obtaining a uterine EMG signal and processing the uterine EMG signal to produce a signal representative of uterine activity. In a first embodiment, the act of processing this uterine EMG signal includes the acts of amplifying the EMG signal, filtering the EMG signal, rectifying the EMG signal to obtain a rectified signal, applying the rectified signal to a peak detector to obtain an analog signal representative of uterine activity, sampling the analog signal representative of uterine activity to obtain data for a digital signal representative of uterine activity, and storing the data of the digital signal representative of uterine activity. In a second embodiment, the act of processing the uterine EMG signal includes the acts of sampling the uterine EMG signal to create a bipolar digital waveform, converting the bipolar digital waveform to a unipolar digital waveform, and time averaging the unipolar digital waveform to obtain the signal representative of uterine activity.

The invention further provides a system for generating a signal representing uterine activity. The system includes a sensor for obtaining a uterine electromyography (EMG) signal, and means for processing the uterine EMG signal to produce a signal representative of uterine activity.

The invention further provides a software program for operating a monitor. The monitor includes a sensor for acquiring a uterine electromyography (EMG) signal and a microprocessor for executing the software program. The software program operates the monitor by sampling the uterine EMG signal to obtain a bipolar digital waveform, and processing the sample uterine EMG signal to produce a signal representative of uterine activity.

Other features and advantages of the invention will become apparent to those skilled in the art upon review of the following detailed description, claims, and drawings.

BRIEF DESCRIPTION OF THE DRAWINGS

FIG. 1 is a chart displaying a typical uterine activity waveform resulting from a toco sensor.

FIG. 3 is a chart displaying a "raw" uterine EMG signal.

FIG. 4 is a chart displaying an equivalent uterine activity waveform.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 2:
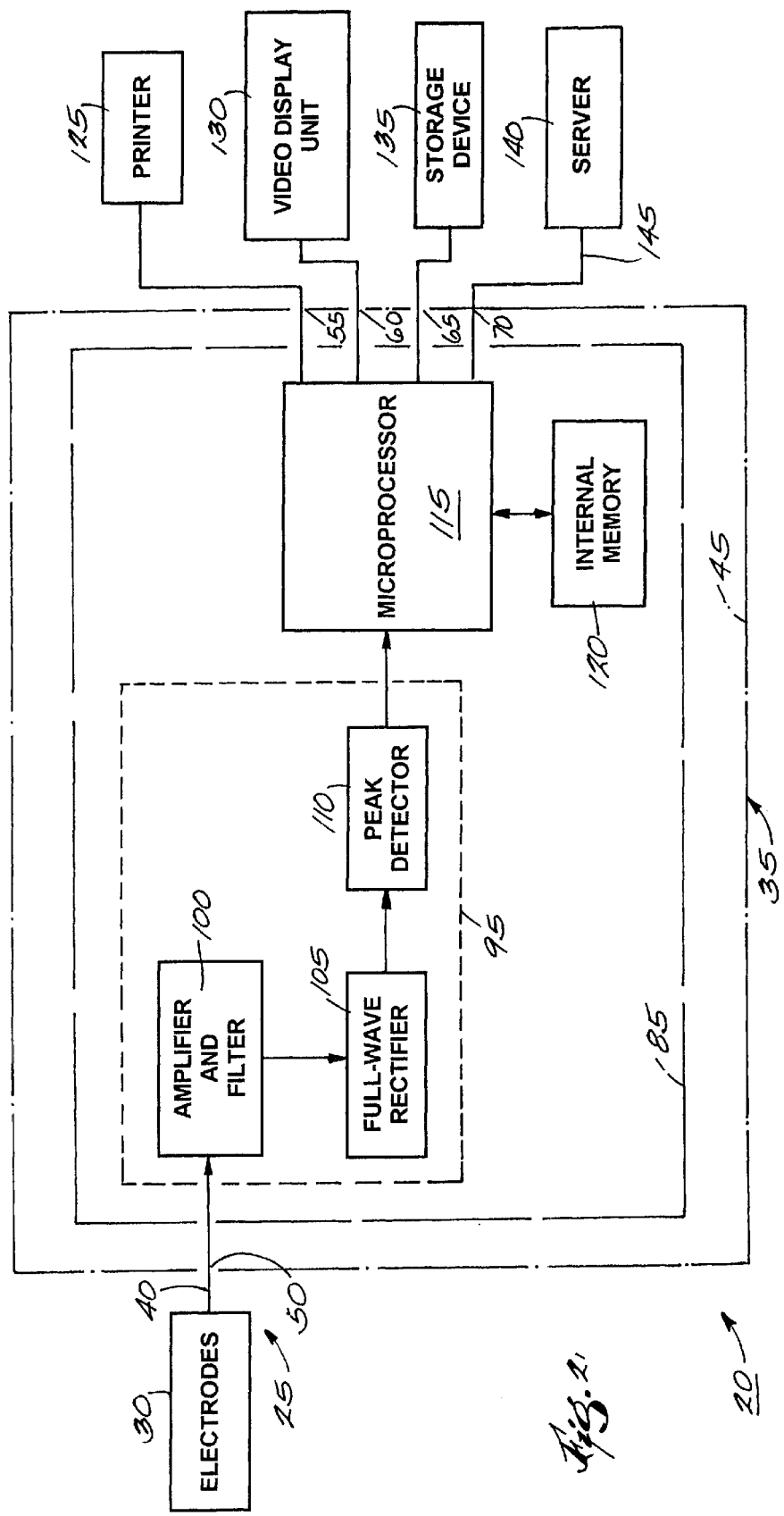
FIG. 2 is a schematic representation of a monitor embodying the invention.

Shown in FIG. 2 of the drawings is a monitor 20 embodying the invention. In general terms, the monitor 20 includes a sensor 25, a central processing unit 35, and output units 125, 130, 135 and/or 140. The sensor 25 acquires a "raw" uterine electromyography (EMG) signal 27 (FIG. 3) from a patient (not shown). The sensor 25 includes one or more pairs of electrodes 30 that are placed on the patient's (i.e., the mother's) abdomen (not shown). The electrodes 30 generate action potentials that are measured differentially across the one or more pairs of electrodes 30 resulting in the raw uterine EMG signal 27. Additional driven or passive electrodes (not shown) may be placed on the patient to establish a reference potential on the patient or to cancel out unwanted common mode signals and noise. The electrodes 30 include lead wires (not shown) that connect to an interface cable 40. The interface cable 40 allows for transmission of the raw uterine EMG signal 27 from the electrodes 30 to the central processing unit 35. The interface cable 40 is preferably a passive cable between the electrodes 30 and the central unit 35. Alternatively, the cable may contain active circuitry (not shown) for amplifying and/or combining lead signals.

The central processing unit 35 has a housing 45. The housing 45 includes communication ports 50, 55, 60, 65 and 70. Additional communication ports can be added as needed.

The central unit 35 includes a signal processor 85, or means for generating a signal representative of uterine activity in response to the uterine EMG signal. The signal processor 85 receives the raw uterine EMG signal from the sensor 25 and processes the uterine EMG signal into a signal representative of uterine activity. The signal representative of uterine activity is printed or displayed on a uterine activity chart 87 (FIG. 4) as an equivalent uterine activity waveform 90 (FIG. 4). The equivalent uterine activity waveform 90 is equivalent to the typical uterine activity waveform 10 (FIG. 1).

As shown in FIG. 2, the signal processor 85 includes a receiver 95 that receives the uterine EMG signal from the sensor 25 and generates an analog signal representative of uterine activity. The receiver includes an amplifier and band-pass filter 100, a full-wave peak rectifier 105 electrically connected to the amplifier and band-pass filter 100, and a peak detector 110 electrically connected to the full wave rectifier 105.

The signal process 85 further includes a microprocessor 115 electrically connected to the receiver 85. The microprocessor 115 receives the analog signal representative of uterine activity and converts the analog signal into a digital signal representative of uterine activity. The signal processor 85 further includes internal memory 120 electrically connected to the microprocessor 115. If only an analog signal representative of uterine activity is desired, then the microprocessor 115 and internal memory 120 are not required. Furthermore, the signal processor 85 can further include addition circuitry (not shown) to perform additional fetal monitoring parameters (e.g., fetal heart rate).

As shown in FIG. 2, output units 125, 130, 135 and 140 are connected to the central unit 35 at communication ports 55, 60, 65 and 70. The output units include a printer 125, a video display unit 130, a storage device 135 (e.g., magnetic disc drive, read/write CD-ROM, etc.), and a server 140 or other processing unit (e.g., a personal computer). The server 140 is connected via a distributed network 145. Of course, other output units can be attached or the output units (e.g., the visual display unit 130) can be incorporated within the central unit 35. Additionally, not all of the output units are required for operation of the monitor.

In operation, the electrodes 30 of the sensor 25 are connected to a patient (not shown). The electrodes 30 obtain a raw uterine EMG signal 27 (FIG. 3) that is transmitted to the signal processor 85 of the control unit 45 via interface cable 40. Upon receiving the raw EMG signal from the sensor 25, the signal processor 85 processes the signal to create a signal representative of uterine activity. The resulting signal representative of uterine activity can be stored in internal memory 123, printed by the printer 125, displayed on the visual display unit 130, stored in storage device 135, and/or provided by communication link 145 to another computer or server 140. The signal representative of uterine activity is displayed or printed on a uterine activity chart 87 as an equivalent uterine activity waveform 90 as shown in FIG. 4. The equivalent uterine activity waveform 90 is representative of a typical uterine activity waveform 15 (FIG. 1) generated by a toco or is representative of at least one component of a typical uterine activity waveform (not shown) generated by a IUP sensor.

For the embodiment shown in FIG. 2, the signal processor 85 processes the raw uterine EMG signal 22 by first providing the signal to the receiver 95. Upon receiving the raw uterine EMG signal 22, the receiver 95 generates an analog signal representative of uterine activity. This is accomplished by first providing the acquired raw uterine EMG signal to the amplifier and band-pass filter 100 to create a processed uterine EMG signal. Amplifying and filtering the raw uterine EMG signal distinguishes the EMG signal from other biological signals and noise sources. After amplifying and filtering the raw EMG signal, the processed EMG signal is provided to the full-wave rectifier 105. The full-wave rectifier 105 inverts the negative portion of the processed EMG signal resulting in a rectified signal. The rectified signal is then applied to the peak detector 110. The peak detector 110 generates a peak value signal having the peak values of the rectified signal. The generated peak value signal is the analog signal representative of uterine activity.

The signal processor 85 shown in FIG. 2 further processes the EMG signal by creating a digital signal representative of uterine activity from the analog signal representative of uterine activity. To create the digital signal representative of uterine activity, the peak value signal is provided to the microprocessor 115. The microprocessor 115 receives the peak value signal and samples the peak value signal. After sampling the peak value signal, the microprocessor 115 temporarily holds or stores the sampled signal in internal memory 120. As the signal is being sampled or after the signal has finished being sampled, the microprocessor 115 scales the data for displaying, printing, storing or transmitting the sampled signal. The microprocessor 115 scales the sampled data to a scale that is comparable to a typical uterine activity chart 10. In other words, by scaling the sampled data, the scaled data, when displayed, appears to a user to approximate a typical uterine activity waveform. After the data has been scaled, the resulting scaled data can be printed in hardcopy by the printer 135, displayed on the visual display unit 130, stored in the storage device 135, or provided to the server 140 via the distributed network 145.

The resulting scaled data provides a digital signal that, when viewed by an operator (e.g., on a visual display), is substantially equivalent to the uterine activity waveform 90 as shown in FIG. 4.

Figure 5:
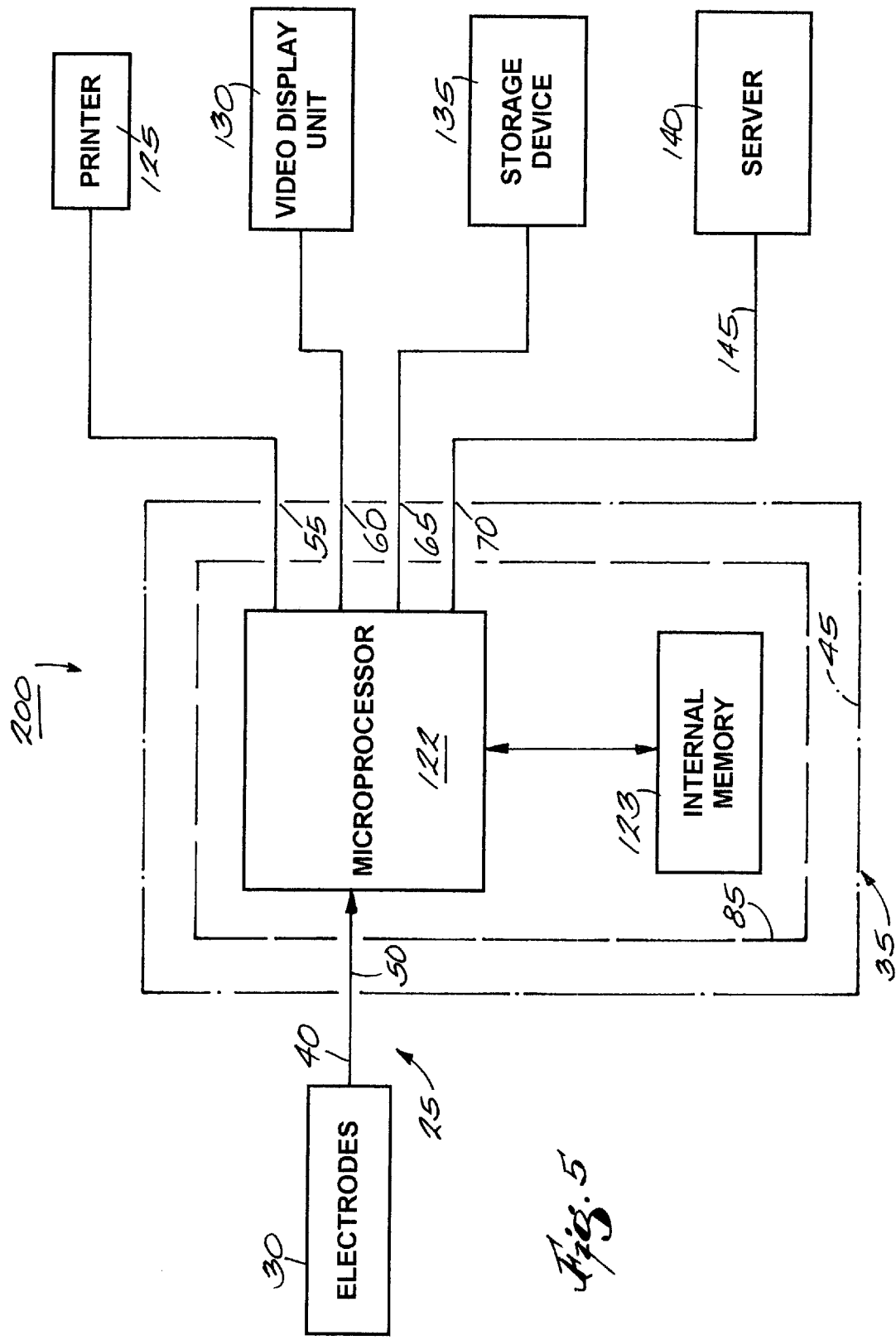
FIG. 5 is a schematic representation of a monitor embodying the invention.

FIG. 5 illustrates a monitor 200, which is an alternative embodiment of the invention. Like parts are identified using like reference numerals. As shown in FIG. 5, the signal processor 85 includes a microprocessor 122 and internal memory 123. In this embodiment, the microprocessor 122 receives a uterine EMG signal and generates a signal representative of uterine activity. The received uterine EMG signal can be either the raw uterine EMG signal 27 from the electrodes 30 or can be a processed uterine EMG signal resulting from an amplifier and filter (not shown). Upon receiving the uterine EMG signal, the microprocessor 122 executes digital processing software that processes the received EMG signal resulting in the signal representative of uterine activity.

For the embodiment shown in FIG. 5, the signal processor 85 processes the raw EMG signal 27 by first providing the signal to microprocessor 122 (assuming an amplifier and filter is not present). The microprocessor 122 samples the raw EMG signal for digital signal processing and stores the sampled data in internal memory 123. When executing the digital signal processing software, the microprocessor 122 first digitally filters the raw EMG signal 27 from other biological signals and noise sources. The filtering of the EMG signals is accomplished by spectral analysis techniques, wavelet analysis techniques, recognition of EMG wave characteristics, and/or cross signal verification techniques.

If the signal processor 85 shown in FIG. 5 includes an amplifier and filter (not shown), then the raw EMG signal 27 is first provided to the amplifier and filter. The amplifier and filter performs the same function as the amplifier and filter 100 of FIG. 2 resulting in a processed uterine EMG signal. The processed uterine EMG signal is then provided to the microprocessor 123 where the microprocessor 123 samples the processed signal for digital signal processing.

Once the raw uterine EMG signal has been amplified and filtered, the microprocessor 122 processes the signal to produce an equivalent uterine activity waveform 90. One possible digital signal processing technique performs a bipolar to unipolar conversion (similar to rectifier 105) and a time averaging of the converted waveform with adjustments made to the presented uterine contraction intensity based on signal characteristics (similar to the peak detector 110). The microprocessor 122 then scales the data to a scale that is comparable to a typical uterine activity chart 10. After the data has been scaled, the resulting signal can be printed in hardcopy by the printer 135, displayed on the visual display unit 130, stored in the storage device 135 or provided to the server 140 via the distributed network 145.

The uterine activity monitor and method of operation of the uterine activity monitor should be apparent from the description and drawings herein and additional details are not provided. Many possible forms of the invention may be constructed based on the teachings set forth herein. Therefore, while the present invention has been described in reference to particular embodiments and examples, it should be understood that the invention is not confined to the particular construction and arrangement of the components illustrated and described, but embraces all forms encompassed by the following claims.

What is claimed is:

1. A method of generating a signal representing uterine activity, the method comprising:

obtaining a uterine electromyography (EMG) signal;

processing the uterine EMG signal to produce a signal representative of uterine activity; and wherein the act of processing the uterine EMG signal comprises the acts of:

sampling the uterine EMG signal to create a bipolar digital waveform;

converting the bipolar digital waveform to a unipolar digital waveform; and time averaging the unipolar digital waveform to obtain the signal representative of uterine activity.

2. A method as set forth in claim 1, wherein the signal representative of uterine activity indicates uterine contraction duration.

3. A method as set forth in claim 1, wherein the signal representative of uterine activity indicates uterine contraction frequency.

4. A method as set forth in claim 1, wherein the signal representative of uterine activity approximates at least one component of a signal that would be acquired using an intrauterine pressure sensor.

5. A method as set forth in claim 1, wherein the signal representative of uterine activity approximates a signal that would be acquired using a tocodynomometer.

6. A method as set forth in claim 1, wherein the act of processing the uterine EMG signal comprises the acts of:

amplifying the uterine EMG signal; and filtering the uterine EMG signal.

7. A method as set forth in claim 1, wherein the act of processing the uterine EMG signal further comprises the acts of:

scaling the signal representative of uterine activity; and storing the signal representative of uterine activity.

8. A method of generating a signal representing uterine activity, the method comprising:

obtaining a uterine electromyography (EMG) signal;

processing the uterine EMG signal to produce a signal representative of uterine activity; and wherein the act of processing the uterine EMG signal further comprises the acts of:

rectifying the uterine EMG signal to obtain a rectified signal; and applying the rectified signal to a peak detector to obtain the signal representative of uterine activity.

9. A method as set forth in claim 8, wherein the signal obtained from the peak detector is an analog signal representative of uterine activity, and wherein the act of processing the uterine EMG signal further comprises the acts of:

sampling the analog signal representative of uterine activity to obtain data for a digital signal representative of uterine activity; and storing the data of the digital signal representative of uterine activity.

10. A method as set forth in claim 9, wherein the act of processing the uterine EMG signal further comprises the acts of:

scaling the data of the digital signal representative of uterine activity; and displaying the digital signal representative of uterine activity.

11. A method as set forth in claim 8, wherein the signal representative of uterine activity indicates uterine contraction duration.

12. A method as set forth in claim 8, wherein the signal representative of uterine activity indicates uterine contraction frequency.

13. A method as set forth in claim 8, wherein the signal representative of uterine activity approximates at least one component of a signal that would be acquired using an intrauterine pressure sensor.

14. A method as set forth in claim 8, wherein the signal representative of uterine activity approximates a signal that would be acquired using a tocodynomometer.

15. A method as set forth in claim 8, wherein the act of processing the uterine EMG signal comprises the acts of:
   amplifying the uterine EMG signal; and
   filtering the uterine EMG signal.

16. A monitor comprising:
   a sensor for acquiring a uterine electromyography (EMG) signal;
   a signal processor for generating a signal representative of uterine activity in response to the uterine EMG signal;
   wherein the signal processor comprises:
      a receiver that receives the uterine EMG signal from the sensor and generates an analog signal representative of uterine activity; and
   wherein the receiver comprises:
      an amplifier and filter for amplifying and filtering the received uterine EMG signal to generate a processed uterine EMG signal;
      a full wave rectifier electrically connected to the amplifier and filter, the full wave rectifier rectifies the processed uterine EMG signal from the amplifier and filter to generate a rectified signal; and
      a peak detector electrically connected to the full wave rectifier for generating a peak value signal having the peak values of the rectified signal, the generated peak value signal is the analog signal representative of uterine activity.

17. A monitor as set forth in claim 16, wherein the signal representative of uterine activity indicates uterine contraction duration.

18. A monitor as set forth in claim 16, wherein the signal representative of uterine activity indicates uterine contraction frequency.

19. A monitor as set forth in claim 16, wherein the signal representative of uterine activity approximates at least one component of a signal that would be acquired using an intrauterine pressure sensor.

20. A monitor as set forth in claim 16, wherein the signal representative of uterine activity approximates a signal that would be acquired using a tocodynomometer.

21. A monitor as set forth in claim 16, wherein the signal processor further comprises:
   a microprocessor electrically connected to the receiver for receiving the analog signal representative of uterine activity and converting the analog signal representative of uterine activity into a digital signal representative of uterine activity; and
   a memory unit electrically connected to the microprocessor for storing the digital signal representative of uterine activity.

22. A monitor comprising:
   a sensor for acquiring a uterine electromyography (EMG) signal;
   a signal processor for generating a signal representative of uterine activity in response to the uterine EMG signal; and
   wherein the signal processor further comprises:
      an amplifier and filter for amplifying and filtering the received uterine EMG signal to generate a processed uterine EMG signal;
      a microprocessor that receives the processed uterine EMG signal and generates the signal representative of uterine activity, the microprocessor generating the signal representative of uterine activity by sampling the processed uterine EMG signal to create a bipolar digital waveform, converting the bipolar digital waveform to a unipolar digital waveform, and time averaging the unipolar digital waveform to obtain the signal representative of uterine activity; and
      a memory unit electrically connected to the microprocessor for storing the signal representative of uterine activity.

23. A monitor as set forth in claim 22, wherein the signal representative of uterine activity indicates uterine contraction duration.

24. A monitor as set forth in claim 22, wherein the signal representative of uterine activity indicates uterine contraction frequency.

25. A monitor as set forth in claim 22, wherein the signal representative of uterine activity approximates at least one component of a signal that would be acquired using an intrauterine pressure sensor.

26. A monitor as set forth in claim 22, wherein the signal representative of uterine activity approximates a signal that would be acquired using a tocodynomometer.

27. A system for generating a signal representing uterine activity, the system comprising:
   a sensor for obtaining a uterine electromyography (EMG) signal; and
   means for processing the uterine EMG signal to produce a signal representative of uterine activity,
   wherein the processing means comprises:
      means for sampling the processed uterine EMG signal to create a bipolar digital waveform;
      means for converting the bipolar digital waveform to a unipolar digital waveform; and
      means for time averaging the unipolar digital waveform to obtain the signal representative of uterine activity.

28. A system as set forth in claim 27, wherein the signal representative of uterine activity indicates uterine contraction duration.

29. A system as set forth in claim 27, wherein the signal representative of uterine activity indicates uterine contraction frequency.

30. A system as set forth in claim 27, wherein the signal representative of uterine activity approximates at least one component of a signal that would be acquired using an intrauterine pressure sensor.

31. A system as set forth in claim 27, wherein the signal representative of uterine activity approximates a signal that would be acquired using a tocodynomometer.

32. A system as set forth in claim 27, wherein the means for processing the uterine EMG signal comprises:
   means for generating an analog signal representative of uterine activity in response to a received uterine EMG signal.

33. A system as set forth in claim 32, wherein the means for processing the uterine EMG signal comprises:
   means for converting the analog signal representative of uterine activity to a digital signal representative of uterine activity; and
   means for storing the digital representative signal.

34. A software program for operating a monitor, the monitor including a sensor for acquiring a uterine electromyography (EMG) signal and a microprocessor for executing the software program, the software program operating the monitor by:

sampling the uterine EMG signal to obtain a bipolar digital waveform;

processing the uterine EMG signal to produce a signal representative of uterine activity; and wherein the act of processing the uterine EMG signal further comprises the acts of:

converting the bipolar digital waveform to a unipolar digital waveform; and time averaging the unipolar digital waveform to obtain the signal representative of uterine activity.

35. A software program as set forth in claim 34, wherein the signal representative of uterine activity indicates uterine contraction duration.

36. A software program as set forth in claim 34, wherein the signal representative of uterine activity indicates uterine contraction frequency.

37. A software program as set forth in claim 34, wherein the signal representative of uterine activity approximates at least one component of a signal that would be acquired using an intrauterine pressure sensor.

38. A software program as set forth in claim 34, wherein the signal representative of uterine activity approximates a signal that would be acquired using a tocodynomometer.

39. A method of generating a signal representing uterine activity, the method comprising:

obtaining a uterine electromyography (EMG) signal;

amplifying the EMG signal;

filtering the EMG signal;

rectifying the EMG signal to obtain a rectified signal;

applying the rectified signal to a peak detector to obtain an analog signal representative of uterine activity;

sampling the analog signal representative of uterine activity to obtain data for a digital representative signal;

scaling the data of the digital signal representative of uterine activity; and displaying the digital signal representative of uterine activity.

40. A method as set forth in claim 39, wherein the signal representative of uterine activity approximates at least one component of a signal that would be acquired using an intrauterine pressure sensor.

41. A method as set forth in claim 39, wherein the signal representative of uterine activity approximates a signal that would be acquired using a tocodynomometer.

42. A monitor comprising:

a sensor for acquiring a uterine electromyography (EMG) signal;

a signal processor for generating a signal representative of uterine activity in response to the uterine EMG signal, the signal representative of uterine activity indicates uterine contraction duration and uterine contraction frequency, the signal comprises:

a receiver for receiving the uterine EMG signal and generating an analog signal representing of uterine activity;

a microprocessor electrically connected to the receiver for receiving the analog signal representative of uterine and converting the analog signal representative of uterine activity into a digital signal representative of uterine activity; and a memory unit electrically connected to the microprocessor for storing the digital signal representative of uterine activity; and wherein the receiver comprises:

an amplifier and filter for amplifying and filtering the received uterine EMG signal;

a full wave rectifier electrically connected to the amplifier and filter, the full wave rectifier rectifies the resultant signal from the amplifier and filter to generate a rectified signal; and a peak detector electrically connected to the fill wave rectifier for generating a peak value signal having the peak values of the rectified signal, the generated peak value signal is the analog signal representative of uterine activity.

43. A monitor as set forth in claim 42, wherein the signal representative of uterine activity approximates at least one component of a signal that would be acquired using an intrauterine pressure sensor.

44. A monitor as set forth in claim 42, wherein the signal representative of uterine activity approximates a signal that would be acquired using a tocodynomometer.

* * * * *

UNITED STATES PATENT AND TRADEMARK OFFICE
CERTIFICATE OF CORRECTION

PATENT NO.     : 6,421,558 B1
DATED          : July 16, 2002
INVENTOR(S)    : Raymond J. Huey et al.

It is certified that error appears in the above-identified patent and that said Letters Patent is hereby corrected as shown below:

<u>Column 10,</u>
Line 11, insert the word "processor" after the word "signal."
Line 13, "representing" should be -- representative. --

Signed and Sealed this

Twenty-sixth Day of November, 2002

*Attest:*

*Attesting Officer*

JAMES E. ROGAN
*Director of the United States Patent and Trademark Office*